United States Patent [19]

Cowper

[11] Patent Number: 5,875,787
[45] Date of Patent: Mar. 2, 1999

[54] HAIRPIECE RETENTION DEVICE AND SYSTEM

[75] Inventor: Thomas R. Cowper, Chesterland, Ohio

[73] Assignee: The Cleveland Clinic Foundation, Cleveland, Ohio

[21] Appl. No.: 429,948

[22] Filed: Apr. 27, 1995

[51] Int. Cl.[6] .................................................. A51G 3/00
[52] U.S. Cl. ............................................ 132/53; 623/15
[58] Field of Search .................................. 132/53, 54, 55, 132/201; 24/694, 589, 588, 629, 630; 623/15

[56] References Cited

U.S. PATENT DOCUMENTS

| | | | |
|---|---|---|---|
| 1,693,514 | 11/1928 | Johnson | 24/694 |
| 3,162,203 | 12/1964 | Cramer . | |
| 3,589,376 | 6/1971 | Kohler . | |
| 3,651,820 | 3/1972 | Johnson et al. . | |
| 3,654,935 | 4/1972 | Brown . | |
| 3,659,621 | 5/1972 | Tucciarone et al. . | |
| 3,662,766 | 5/1972 | Maassen et al. | 132/201 |
| 3,672,362 | 6/1972 | Basché . | |
| 3,694,819 | 10/1972 | Meyer . | |
| 3,724,470 | 4/1973 | Wilson . | |
| 3,811,425 | 5/1974 | Widdifield . | |
| 3,862,453 | 1/1975 | Widdifield . | |
| 3,889,695 | 6/1975 | Incando . | |
| 3,896,821 | 7/1975 | Clark . | |
| 3,908,674 | 9/1975 | Kessler | 132/53 |
| 4,050,100 | 9/1977 | Barry . | |
| 4,144,794 | 3/1979 | Silverman et al. | 24/694 |
| 4,155,370 | 5/1979 | Nemoto . | |
| 4,265,246 | 5/1981 | Barry . | |
| 4,360,033 | 11/1982 | Schmehling . | |
| 4,667,664 | 5/1987 | Taylor et al. . | |
| 4,753,656 | 6/1988 | Tofiled et al. | 623/15 |
| 4,771,798 | 9/1988 | Candino . | |
| 4,918,757 | 4/1990 | Janssen et al. . | |
| 5,212,720 | 5/1993 | Landi et al. . | |
| 5,303,723 | 4/1994 | Schach . | |

FOREIGN PATENT DOCUMENTS

| | | | |
|---|---|---|---|
| 2373271 | 8/1978 | France | 132/201 |

OTHER PUBLICATIONS

A. Pignataro and N., Schaaf, "A New Method of Hair Replacement Using Osseointegrated Prostheses", *The American Journal of Cosmetic Surgery*, vol. 11, No. 2, 1994.

*Primary Examiner*—Todd E. Manahan
*Attorney, Agent, or Firm*—Fay, Sharpe, Beall, Fagan, Minnich & McKee

[57] ABSTRACT

A device attaches a hairpiece to a human head. The device includes 1.) a fixture implanted in the skull bone, 2.) a sleeve, defining a female receptacle extending from the fixture through the scalp for a distance equal to a thickness of the scalp, and 3.) a male connector attachable to a hairpiece at one end and receivable in the female receptacle at the other. The hairpiece is thus conveniently snap-fit onto the head of the user through the use of a plurality of these devices.

17 Claims, 2 Drawing Sheets

HAIRPIECE RETENTION DEVICE AND SYSTEM

BACKGROUND OF THE INVENTION

This invention relates to a device and system for retaining a hairpiece on a human head. More particularly, the invention is directed to a device including an assembly partially implanted into the skull bone which receives a male connector attached to the hairpiece itself. A plurality of these devices are arranged to retain a hairpiece at a plurality of points.

While the invention is particularly directed to the art of hairpiece retention, and will be thus described with specific reference thereto, it will be appreciated that the invention may have usefulness in other fields and applications.

Hairpieces, or toupees, are commonly worn. However, a well recognized problem with hairpieces is a lack of reliable techniques for retaining these items on the head of the user. Adhesives and weaves have been used in attempts to secure hairpieces. For a variety of reasons, however, these techniques oftentimes fail and, thus, do not meet the expectations of the user.

A variety of other mechanisms which anchor hairpieces to scalps have been contemplated. For example, U.S. Pat. No. 3,694,891 to Meyer is directed to a hairpiece securing device comprised of 1.) an anchor which is surgically imbedded in the scalp, partially under the aponeurosis, and 2.) an attachment piece which is removeably attached to the anchor by latching means. Additionally, U.S. Pat. No. 3,862,453 to Widdifield, U.S. Pat. No. 3,811,425 to Widdifield, U.S. Pat. No. 4,050,100 to Barry, and U.S. Pat. No. 4,265,246 to Barry, all describe hairpiece retention techniques incorporating some type of anchoring to the scalp.

Moreover, maxillofacial prostheses are known. Like conventional hairpieces, the retention of maxillofacial prostheses has been a problem for users thereof. Traditionally, various mechanical devices or adhesives systems have been used with varying success. Chief among the problems is the weakening of the retentive mechanism during normal day-to-day activities. A further problem for both operator and patient is the time and manual dexterity required to apply the adhesive systems and the restoration to the intended site. Furthermore, the use of adhesives accelerates the wear and tear on the prostheses and shortens its effective life span.

Bone anchored craniofacial implants, although early in development, have shown potential to reduce these problems. The general international experience with craniofacial implants has been limited to sites on the human head where traditional maxillofacial prostheses have been employed. That is, bone anchored craniofacial implants have typically been implanted in the mastoid process of the temporal bone, fronto-orbital region, and the nasal bones. One known commercially available craniofacial implant system is the Bud Implant System used in maxillofacial prosthetic restorations.

A recent article, A. S. Pignataro, M. D. and N. G. Schaaf, D. D. S., "A New Method of Hair Replacement using Osseointegrated Prostheses," *The American Journal of Cosmetic Surgery*, Vol. 11, No. 2 (1994), describes a craniofacial implant mechanism implanted into the skull bone to retain a hairpiece on the head of a user. The device described, however, uses an implant abutment which protrudes 1–2 millimeters above the scalp. A male attachment is also fitted into the abutment so that a hairpiece can be secured to the head. A major disadvantage of this system is that the abutment, and, to a greater extent, the male portion protruding from the abutment, extends radially outwardly from the head. This extension is neither aesthetically pleasing nor safe.

The present invention contemplates a new and improved hairpiece retention device and system which resolves the above-referenced difficulties and others.

SUMMARY OF THE INVENTION

A device for attaching a hairpiece to a human head is provided. A fixture is implanted in the skull bone. A sleeve, defining a female receptacle, extends from the fixture through the scalp for a distance approximately equal to the thickness of the scalp.

In accordance with another aspect of the present invention, a male connector, attachable to a hairpiece at one end and receivable in the female receptacle at the other, is used to attach the hairpiece to the human head.

In accordance with another aspect of the present invention, the sleeve has a groove disposed about an inner surface thereof which has an O-ring disposed therein to retain the male connector when received in the sleeve.

In accordance with another aspect of the invention, a fastener is disposed through a cylinder in the sleeve and received in a channel of the fixture to connect the sleeve to the fixture.

In accordance with another aspect of the invention, the fixture comprises a flange which prevents implantation of the fixture beyond a predetermined distance.

In accordance with another aspect of the invention, the sleeve and fixture are formed of titanium.

In accordance with another aspect in the invention, a hairpiece retention system comprises a hairpiece having attached thereto a plurality of male connectors and a plurality of corresponding implant assemblies implanted in the head.

In accordance with another aspect of the present invention, plugs resembling the scalp or hair, are provided to be inserted in the sleeves during the time when a hairpiece is not being used.

One advantage of the present invention is that it provides longer, more effective retention through the use of an O-ring and male connector.

Another advantage of the present invention is the increased ease in application and removal of the hairpiece through simpler attachment techniques.

Another advantage of the present invention is that the fixture and sleeve do not protrude beyond the scalp surface.

Another advantage of the present invention is that when a hairpiece is not being retained, plugs, resembling the scalp or hair, are inserted into the sleeves for both aesthetic and hygienic reasons.

Still further advantages of the present invention will become apparent to those of ordinary skill in the art upon reading and understanding the following detailed description of the preferred embodiments.

BRIEF DESCRIPTION OF THE DRAWINGS

The present invention exists in the construction, arrangement, and combination of the various parts of the device, whereby the objects contemplated are attained as hereinafter more fully set forth, specifically pointed out in the claims, and illustrated in the accompanying drawings, in which:

DETAILED DESCRIPTION OF THE PREFERRED EMBODIMENTS

Figure 1:
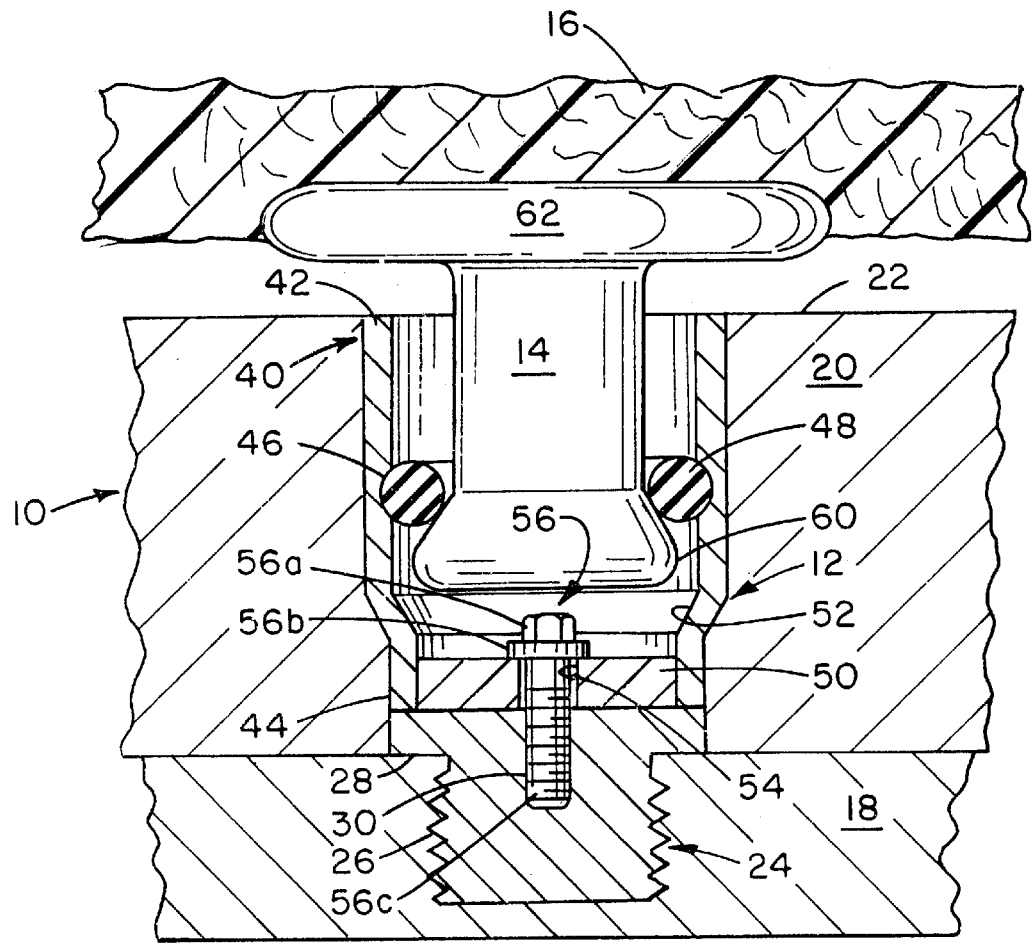
FIG. 1 is a side cross-sectional view of the hairpiece retention device herein contemplated.

Referring now to the drawings wherein the showings are for purposes of illustrating the preferred embodiments of the invention only, and not for purposes of limiting same, FIG. 1 provides a view of a hairpiece retention device 10 used in a system to secure a hairpiece to a human head. As will be described with reference to FIGS. 2 and 3, a plurality of devices 10 are utilized in the system.

The device 10 includes an implant assembly 12 which receives a male connector 14 attached to a hairpiece 16. The implant assembly 12 extends from the skull bone 18 through the scalp 20 and terminates at the scalp surface 22.

The implant assembly 12 comprises a fixture 24 which has a threaded portion 26, flange 28, and channel 30. The fixture 24 is implanted into the skull bone 18 using known medical techniques. Typically, a CT scan is performed to determine whether sufficient bone material is present in the head to bore a hole in the skull bone to place an implant. Once the hole is bored, the threaded portion 26, which is substantially cylindrical and has a diameter of approximately 3.20 millimeters, is implanted in the hole. The flange 28 is circumferentially disposed about an end of the fixture 24 to prevent intracranial penetration of the fixture. The fixture 24 is thus preferably only placed 3.50 millimeters into the skull bone.

The channel 30 is provided to the fixture 24 on the same end as the flange 28. The channel 30 receives a fastener, as will be described below.

The implant assembly 12 further includes an abutment sleeve 40 having a first open cylindrical end 42 and a second closed cylindrical end 44. The first end 42 is approximately 5.5 millimeters in diameter while the second end 44 is approximately 4.5 millimeters in diameter. The sleeve 40 also has a groove 46 disposed on an inner surface 52 thereof. The groove 46 retains an O-ring 48.

The first end 42 defines a female receptacle to receive the male connector 14. The second end 44 has bonded thereto a disk-like metal cylinder 50 to facilitate attachment to the fixture 24. The cylinder 50 includes an aperture 54 and is bonded along its periphery to the inner surface 52.

The sleeve 40 is connected to the fixture 24 via a fastener, or screw, 56. The fastener 56 preferably includes a hex head 56a adapted to accept a wrench driver (not shown), an enlarged portion 56b and a threaded portion 56c that extends through the aperture 54 of the cylinder 50 and is threadingly received into channel 30. Any suitable fastener may be alternatively used.

It is significant to emphasize that the combination of the sleeve 40 and the fixture 24, as noted above, do not protrude beyond the scalp surface. As a result, the user does not have any unnecessary abutment or stud extending from his/her head, which abutment or stud may cause discomfort or inconvenience to the user.

The male connector 14 includes a bulbous end 60 which cooperates with O-ring 48 so that the connector 14 is retained within the sleeve 40. More particularly, the end 60 is sized to allow it to engage the O-ring during insertion, yet still pass through the O-ring 48 upon exertion of sufficient force. This arrangement essentially provides a snap-fit between the sleeve/O-ring combination and the male connector. As is appreciated by those skilled in the art, the male connector 14 will be retained within the sleeve until such time as a force equivalent to the insertion force is exerted on the connector 14 to remove it from the sleeve.

The opposite end 62 of the male connector 14 is bonded to the hairpiece 16. Any suitable bonding technique may be used. Alternatively, the hairpiece can be connected to the male connector end 62 by other known techniques such as sewing, velcro use, etc.

Figure 2:
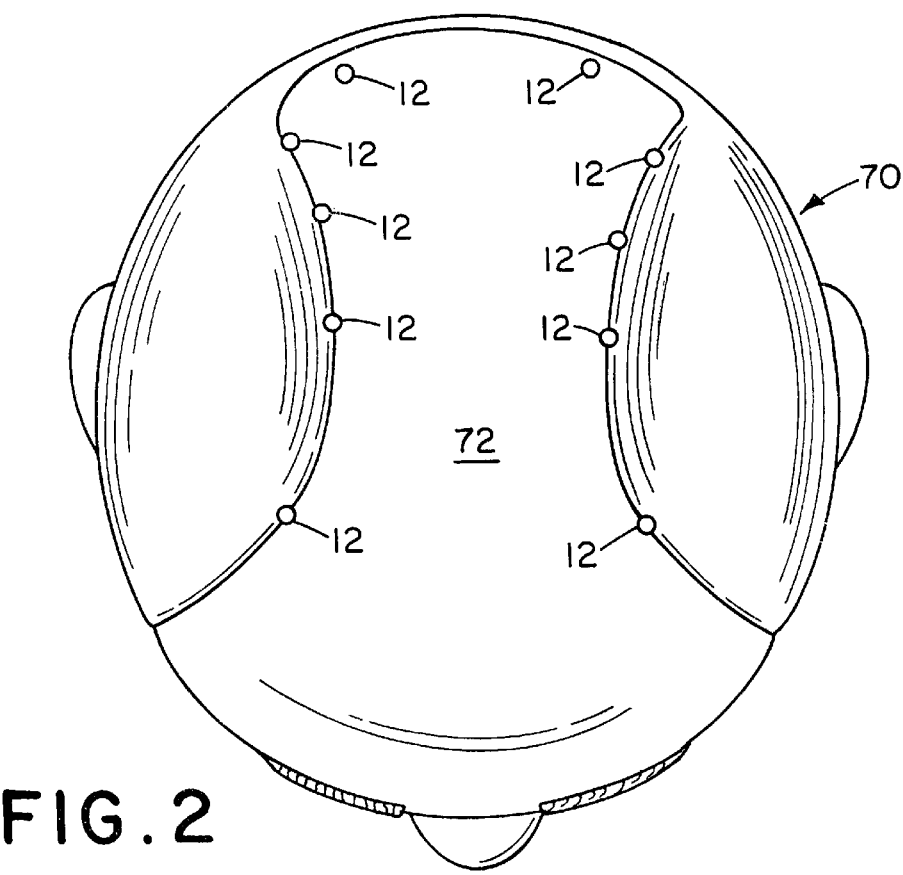
FIG. 2 is a top view of a human head incorporating the implant assemblies of the device of FIG. 1.

Referring now to FIG. 2, a human head 70 is shown. The head 70 includes a bald area 72 which has disposed therearound a predetermined number of implant assemblies 12. The implant assemblies 12 are implanted in a predetermined pattern on the head 70. Both the number of assemblies 12 implanted and the pattern thereof are determined by the needs of the user and accepted medical and surgical protocols.

Figure 3:
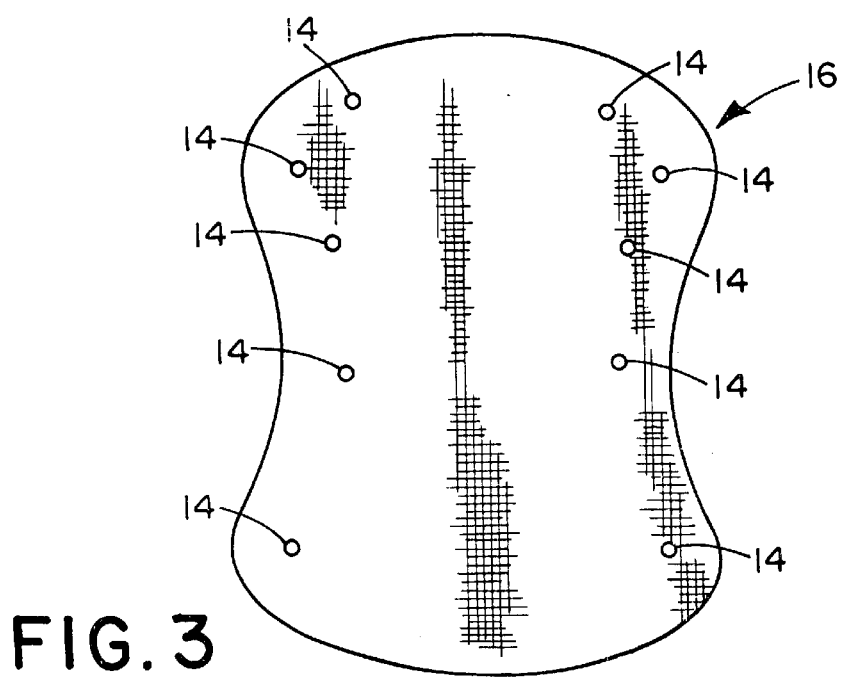
FIG. 3 is a back elevational view of a hairpiece incorporating the male connectors of FIG. 1.

FIG. 3 shows the backside of the hairpiece 16 having a plurality of male connectors 14 bonded thereto. The male connectors 14 are positioned in an identical predetermined pattern as those of implant assemblies 12 in FIG. 2. One-to-one correspondence between the male connectors 14 and implant assemblies 12, along with an identical pattern of placement, facilitates convenient attachment.

Figure 4:
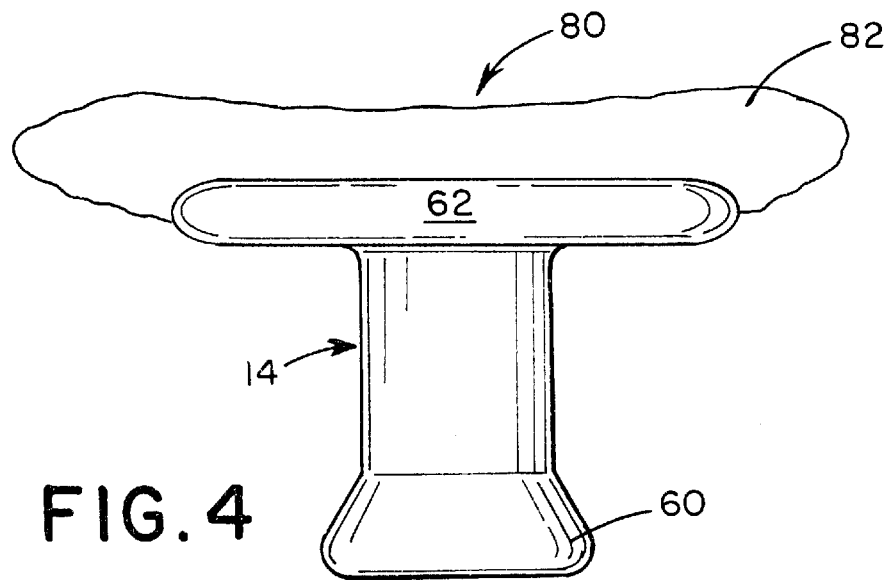
FIG. 4 is a side view of a plug according to the present invention.

Referring now to FIG. 4, a plug 80 includes a male connector 14 having a swatch of imitation scalp material or replacement hair 82 attached to end 62. The plug 80 is inserted and snap-fit into the sleeve 40 when the hairpiece 16 is not being used. The female receptacle of sleeve 40 is thus camouflaged. The plug 80 also helps prevent any hygiene problems because it does not allow dirt or other foreign material to enter the sleeve 40.

The plugs 80 are preferably used at all sites of a subassembly 12. Additionally, whether a swatch 82 includes hair or scalp material depends on the location of the corresponding implant assembly 12.

With respect to the material used, the sleeve 40 and fixture 24 are preferably formed of commercially pure titanium. The O-ring 48 is preferably silicone rubber. The male connector 14 is preferably molded plastic. However, any of these materials may be substituted with materials that facilitate achieving the basic goals of the invention described herein.

The above description merely provides a disclosure of particular embodiments of the invention and is not intended for the purpose of limiting the same thereto. As such, the invention is not limited to only the above described embodiments. Rather, it is recognized that one skilled in the art could conceive alternative embodiments that fall within the scope of the invention.

Having thus described the invention, I claim:

1. A device for attaching a hairpiece or swatch of replacement hair or skin to a human head having a skull bone and a scalp, the device comprising:

a fixture configured to be implanted in the skull bone;

a sleeve defining a female receptacle configured to extend from the fixture through the scalp for a distance approximately equal to a thickness of the scalp so that the sleeve does not protrude beyond the scalp; and a male connector configured to be attached to the hairpiece or swatch at one end and received in the female receptacle at another end to attach the hairpiece or swatch to the human head.

2. An apparatus adaptable to retain a hairpiece or a swatch of replacement hair or skin to a human head having a scalp covering a skull bone, the apparatus adapted to be disposed substantially under the scalp and partially implanted in the skull bone, the apparatus comprising:

a cylindrical sleeve having a groove disposed about an inner surface thereof and a cylinder connected therein;

an O-ring disposed in the groove;

a fixture having a channel for receiving a fastener disposed through the cylinder and received in the channel to connect the sleeve to the fixture; and, a connector having the hairpiece or swatch secured to one end, a second end of the connector being receivable within the sleeve and retained therein by the O-ring.

3. The apparatus as set forth in claim 2 further comprising a flange associated with the fixture.

4. The apparatus as set forth in claim 2 wherein the sleeve extends radially from the skull bone and terminates at a surface of the scalp.

5. The apparatus as set forth in claim 2 wherein the sleeve is formed of titanium.

6. The apparatus as set forth in claim 2 wherein the fixture is formed of titanium.

7. The apparatus as set forth in claim 2 wherein the fixture is approximately 3.50 millimeters in length.

8. The apparatus as set forth in claim 2 wherein the fastener is a screw.

9. The apparatus as set forth in claim 2 wherein the connector is a snap connector.

10. A hairpiece retention device for retaining a hairpiece to a human head having a scalp and a skull bone, the device comprising:

a cylindrical abutment sleeve having an inner surface and two ends, the inner surface having a groove formed therein and a first of the two ends having a disk-like cylinder with an aperture therein and bonded along its periphery to the inner surface of the sleeve;

an O-ring disposed in the groove;

an implant fixture implantable in the skull bone, the fixture having a threaded retaining channel and a flange, the flange preventing the fixture from being implanted in the skull bone more than a predetermined distance;

a fastener extending through the aperture of the cylinder and threadingly received in the retaining channel to connect the sleeve to the fixture so that the sleeve radially extends from the fixture and terminates at a second end thereof at a surface of the scalp; and, a male connector having a hairpiece secured to first end, a second end of the connector being receivable in a second of the ends of the sleeve and retained in the sleeve by friction fit with the O-ring.

11. The device as set forth in claim 10 wherein the predetermined distance is approximately 3.50 millimeters.

12. The device as set forth in claim 10 wherein the sleeve is formed of titanium.

13. The device as set forth in claim 10 wherein the fixture is formed of titanium.

14. A combination comprising:

a hairpiece having attached thereto a plurality of male connectors; and, a plurality of implant assemblies corresponding to the plurality of male connectors, each implant assembly including, a sleeve having a female receptacle adapted to receive a male connector and having a groove disposed about an inner surface thereof, an O-ring disposed in the groove to retain a received male connector, a fixture implantable in the human skull bone; and, a fastener connecting the sleeve to the fixture.

15. The combination as set forth in claim 14 wherein the plurality of male connectors is arranged on the hairpiece in a predetermined pattern.

16. The combination as set forth in claim 15 wherein the plurality of implant assemblies is implanted in the skull in the predetermined pattern.

17. The combination as set forth in claim 14 wherein one-to-one correspondence exists between male connectors and implant assemblies.

* * * * *